United States Patent
Edwin et al.

(10) Patent No.: US 6,790,226 B2
(45) Date of Patent: *Sep. 14, 2004

(54) ENDOLUMINAL PROSTHESIS WITH SUPPORT WIRE

(75) Inventors: Tarun J. Edwin, Chandler, AZ (US); Rajagopal R. Kowligi, Phoenix, AZ (US); Brendan J. McCrea, Ballwin, MO (US); Christopher E. Banas, San Antonio, TX (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/858,035

(22) Filed: May 15, 2001

(65) Prior Publication Data

US 2001/0021870 A1 Sep. 13, 2001

Related U.S. Application Data

(60) Division of application No. 09/855,918, filed on May 15, 2001, which is a division of application No. 08/999,583, filed on Dec. 22, 1997, now Pat. No. 6,264,684, and a continuation-in-part of application No. 08/833,797, filed on Apr. 9, 1997, now Pat. No. 6,451,047, and a continuation-in-part of application No. 08/794,871, filed on Feb. 5, 1997, now Pat. No. 6,039,755, which is a continuation-in-part of application No. PCT/US95/16497, filed on Dec. 8, 1995, which is a continuation-in-part of application No. 08/508,033, filed on Jul. 27, 1995, now Pat. No. 5,749,880, which is a continuation-in-part of application No. 08/401,871, filed on Mar. 10, 1995, now Pat. No. 6,124,523.

(51) Int. Cl.⁷ .................................................. A61F 2/06
(52) U.S. Cl. ...................................... 623/1.13; 623/1.22
(58) Field of Search .............................. 623/1.13, 1.27, 623/23.7, 23.71, 1.15, 1.22, 1.14; 606/195, 198, 194, 191

(56) References Cited

U.S. PATENT DOCUMENTS

| 612,897 A | 10/1898 | Ellis |
| 1,505,591 A | 2/1924 | Goldfarb |
| 2,642,625 A | 6/1953 | Peck |

(List continued on next page.)

FOREIGN PATENT DOCUMENTS

| DE | 39 18736 A1 | 12/1990 |
| EP | 0 221 570 A2 | 5/1987 |
| EP | 0 335 341 A1 | 10/1989 |
| EP | 0 335 341 A | 10/1989 |
| EP | 0 461 791 A1 | 12/1991 |
| EP | 0 461 791 A | 12/1991 |
| EP | 0 551 179 A1 | 7/1993 |
| EP | 0 646 365 A1 | 4/1995 |
| EP | 0 648 869 A1 | 4/1995 |
| EP | 0 656 196 A1 | 6/1995 |
| EP | 0 662 307 A1 | 7/1995 |
| EP | 0 667 132 A2 | 8/1995 |

(List continued on next page.)

OTHER PUBLICATIONS

Association for the Advancement of Medical Instrumentation (1994)."Cardiovascular Implants—Vascular prostheses," *ANSI/AAMI VP* 20, pp. i–vi and 1–31.

(List continued on next page.)

*Primary Examiner*—Paul B. Prebilic
(74) *Attorney, Agent, or Firm*—Morrison & Foerster LLP

(57) ABSTRACT

An endoluminal prosthesis for implantation within a body lumen to maintain luminal patency, including a support structure and a polymer component, which may be in the form of a wire member joined to a polymer cladding. The support structure may be formed of shape memory alloys, which exhibit either shape memory or pseudoelastic properties, or from an elastic material having an inherent spring tension such as spring steel, braided stainless steel wire, or composite materials, such as woven or braided carbon fibers. The polymer cladding may be formed from a variety of suitable materials.

14 Claims, 4 Drawing Sheets

U.S. PATENT DOCUMENTS

| | | |
|---|---|---|
| 3,027,601 A | 4/1962 | Barry |
| 3,060,517 A | 10/1962 | Fields |
| 3,196,194 A | 7/1965 | Ely, Jr. et al. |
| 3,281,511 A | 10/1966 | Goldsmith |
| 3,767,500 A | 10/1973 | Tally et al. |
| 3,887,761 A | 6/1975 | Gore |
| 3,992,725 A | 11/1976 | Homsy |
| 4,061,517 A | 12/1977 | Dutton, III et al. |
| 4,159,370 A | 6/1979 | Koizumi et al. |
| RE31,341 E | 8/1983 | Koizumi et al. |
| 4,416,028 A | 11/1983 | Eriksson et al. |
| 4,482,516 A | 11/1984 | Bowman et al. |
| 4,503,569 A | 3/1985 | Dotter |
| 4,512,338 A | 4/1985 | Balko et al. |
| 4,580,568 A | 4/1986 | Gianturco |
| 4,596,837 A | 6/1986 | Yamamoto et al. |
| 4,647,416 A | 3/1987 | Seiler, Jr. et al. |
| 4,655,769 A | 4/1987 | Zachariades |
| 4,665,906 A | 5/1987 | Jervis |
| 4,714,748 A | 12/1987 | Hoashi et al. |
| 4,731,073 A | 3/1988 | Robinson |
| 4,733,665 A | 3/1988 | Palmaz |
| 4,739,762 A | 4/1988 | Palmaz |
| 4,760,102 A | 7/1988 | Moriyama et al. |
| 4,776,337 A | 10/1988 | Palmaz |
| 4,816,339 A | 3/1989 | Tu et al. |
| 4,820,298 A | 4/1989 | Leveen et al. |
| 4,830,062 A | 5/1989 | Yamamoto et al. |
| 4,886,062 A * | 12/1989 | Wiktor .................... 623/1.15 |
| 4,922,905 A | 5/1990 | Strecker |
| 4,935,068 A | 6/1990 | Duerig |
| 4,955,899 A | 9/1990 | Della Corna et al. |
| 4,957,669 A | 9/1990 | Primm |
| 4,969,896 A | 11/1990 | Shors |
| 5,061,276 A | 10/1991 | Tu et al. |
| 5,071,609 A | 12/1991 | Tu et al. |
| 5,078,726 A | 1/1992 | Kreamer |
| 5,084,065 A | 1/1992 | Weldon et al. |
| 5,102,417 A | 4/1992 | Palmaz |
| 5,122,154 A | 6/1992 | Rhodes |
| 5,123,917 A | 6/1992 | Lee |
| 5,135,503 A | 8/1992 | Abrams |
| 5,143,085 A | 9/1992 | Wilson |
| 5,152,782 A | 10/1992 | Kowligi et al. |
| 5,156,620 A | 10/1992 | Pigott |
| 5,163,951 A | 11/1992 | Pinchuk et al. |
| 5,171,805 A | 12/1992 | Tatemoto et al. |
| 5,195,984 A | 3/1993 | Schatz |
| 5,211,658 A | 5/1993 | Clouse |
| 5,219,355 A | 6/1993 | Parodi et al. |
| 5,231,989 A | 8/1993 | Middleman et al. |
| 5,234,739 A | 8/1993 | Tanaru et al. |
| 5,282,848 A | 2/1994 | Schmitt |
| 5,282,860 A | 2/1994 | Matsuno et al. |
| 5,316,023 A | 5/1994 | Palmaz et al. |
| 5,330,500 A | 7/1994 | Song |
| 5,334,201 A | 8/1994 | Cowan |
| 5,341,818 A | 8/1994 | Abrams et al. |
| 5,349,964 A | 9/1994 | Imran et al. |
| 5,354,309 A | 10/1994 | Schnepp-Pesch |
| 5,354,329 A | 10/1994 | Whalen |
| 5,360,443 A | 11/1994 | Barone et al. |
| 5,366,504 A | 11/1994 | Andersen et al. |
| 5,370,681 A | 12/1994 | Herweck et al. |
| 5,370,691 A * | 12/1994 | Samson .................... 623/1.22 |
| 5,376,110 A | 12/1994 | Tu et al. |
| 5,382,261 A | 1/1995 | Palmaz |
| 5,383,926 A | 1/1995 | Lock et al. |
| 5,385,580 A | 1/1995 | Schmitt |
| 5,387,235 A | 2/1995 | Chuter |
| 5,387,236 A | 2/1995 | Noishiki et al. |
| 5,389,106 A | 2/1995 | Tower |
| 5,405,377 A | 4/1995 | Cragg |
| 5,405,378 A | 4/1995 | Strecker |
| 5,411,476 A | 5/1995 | Abrams et al. |
| 5,429,869 A | 7/1995 | McGregor et al. |
| 5,433,996 A | 7/1995 | Kranzler et al. |
| 5,449,373 A | 9/1995 | Pinchasik et al. |
| 5,452,726 A | 9/1995 | Burmeister et al. |
| 5,464,438 A | 11/1995 | Menaker |
| 5,464,440 A | 11/1995 | Johansson |
| 5,464,449 A | 11/1995 | Ryan et al. |
| 5,489,295 A | 2/1996 | Piplani et al. |
| 5,496,364 A | 3/1996 | Schmitt |
| 5,500,013 A | 3/1996 | Buscemi et al. |
| 5,507,769 A | 4/1996 | Marin et al. |
| 5,507,771 A | 4/1996 | Gianturco |
| 5,514,115 A | 5/1996 | Frantzen et al. |
| 5,522,883 A | 6/1996 | Slater et al. |
| 5,523,092 A | 6/1996 | Hanson et al. |
| 5,527,353 A | 6/1996 | Schmitt |
| 5,527,355 A | 6/1996 | Ahn |
| 5,540,712 A | 7/1996 | Kleshinski et al. |
| 5,540,713 A | 7/1996 | Schnepp-Pesch et al. |
| 5,549,663 A | 8/1996 | Cottone |
| 5,556,389 A | 9/1996 | Liprie |
| 5,556,414 A | 9/1996 | Turi |
| 5,562,725 A | 10/1996 | Schmitt |
| 5,571,170 A | 11/1996 | Palmaz et al. |
| 5,571,171 A | 11/1996 | Barone et al. |
| 5,571,173 A | 11/1996 | Parodi |
| 5,591,197 A | 1/1997 | Orth et al. |
| 5,591,222 A | 1/1997 | Susawa et al. |
| 5,591,223 A | 1/1997 | Lock et al. |
| 5,591,224 A | 1/1997 | Schwartz et al. |
| 5,591,228 A | 1/1997 | Edoga |
| 5,591,229 A | 1/1997 | Parodi |
| 5,591,288 A | 1/1997 | Edogn |
| 5,597,378 A | 1/1997 | Jervis |
| 5,620,763 A | 4/1997 | House et al. |
| 5,628,786 A | 5/1997 | Banas et al. |
| 5,628,788 A | 5/1997 | Pinchuk |
| 5,630,806 A | 5/1997 | Inagaki et al. |
| 5,630,829 A | 5/1997 | Lauterjung |
| 5,630,840 A | 5/1997 | Mayer |
| 5,665,117 A | 9/1997 | Rhodes |
| 5,667,523 A | 9/1997 | Bynon et al. |
| 5,674,241 A | 10/1997 | Bley et al. |
| 5,676,671 A * | 10/1997 | Inoue .................... 606/198 |
| 5,681,345 A | 10/1997 | Euteneuer |
| 5,718,159 A | 2/1998 | Thompson |
| 5,723,004 A | 3/1998 | Dereume et al. |
| 5,735,892 A | 4/1998 | Myers et al. |
| 5,749,880 A | 5/1998 | Banas et al. |
| 5,788,626 A | 8/1998 | Thompson |
| 5,800,512 A | 9/1998 | Lentz et al. |
| 5,824,046 A | 10/1998 | Smith et al. |
| 5,824,053 A * | 10/1998 | Khosravi et al. .......... 623/1.15 |
| 5,961,545 A * | 10/1999 | Lentz et al. .............. 623/1.39 |
| 5,968,091 A * | 10/1999 | Pinchuk et al. ............ 623/1.16 |
| 6,001,125 A | 12/1999 | Golds et al. |
| 6,124,523 A | 9/2000 | Banas et al. |
| 6,139,573 A | 10/2000 | Sogard et al. |
| 6,156,062 A * | 12/2000 | McGuinness .............. 623/1.22 |
| 6,165,210 A | 12/2000 | Lau et al. |
| 6,306,141 B1 | 10/2001 | Jervis |
| 6,309,413 B1 | 10/2001 | Dereume et al. |
| 6,312,454 B1 | 11/2001 | Stockel et al. |
| 6,364,904 B1 | 4/2002 | Smith |
| 6,375,787 B1 | 4/2002 | Lukic |
| 6,451,052 B1 | 9/2002 | Burmeister et al. |

| | | | |
|---|---|---|---|
| 6,497,671 B2 | * | 12/2002 | Ferrera et al. ............... 600/585 |
| 6,585,760 B1 | * | 7/2003 | Fogarty ...................... 623/1.22 |

FOREIGN PATENT DOCUMENTS

| | | |
|---|---|---|
| EP | 0 689 805 | 1/1996 |
| EP | 0 689 806 | 1/1996 |
| EP | 0 716 835 | 6/1996 |
| EP | 0 730 848 | 9/1996 |
| EP | 0 747 022 | 12/1996 |
| EP | 0 749 729 | 12/1996 |
| GB | 1 505 591 | 3/1978 |
| WO | WO 94/12136 | 6/1994 |
| WO | WO 95/05132 | 2/1995 |
| WO | WO 95/05277 | 2/1995 |
| WO | WO 95/05555 | 2/1995 |
| WO | WO 95/95132 | 2/1995 |
| WO | WO 96/12517 | 5/1996 |
| WO | PCT/US95/11817 | 7/1996 |
| WO | WO 96/22745 | 8/1996 |
| WO | WO 96/25897 | 8/1996 |
| WO | WO 96/33066 | 10/1996 |
| WO | WO 96/37165 | 11/1996 |
| WO | WO 96/40000 | 12/1996 |
| WO | WO 97/21401 | 6/1997 |
| WO | WO 98/00090 | 1/1998 |
| WO | WO 98/26731 | 6/1998 |
| WO | WO 98/31305 | 7/1998 |
| WO | WO 98/31306 | 7/1998 |
| WO | WO 98/38947 | 9/1998 |

OTHER PUBLICATIONS

Chuter, T. (1994). "Bifurcated endovascular graft insertion for abdominal aortic aneurysm," *Vascular and Endovascular Surgical Techniques*. 3rd Edition, R. M. Greenhalgh ed., W. B. Saunders Company Ltd.: Philadelphia , pp. 92–99.

Cragg, A. and Dake, M. (Jun. 1993). "Persutaneous Femoropopliteal Graft Placement," *Interventional Radiology* 187(30: 643–648.

Dietrich, E. and Papazoglou, K. (1995). Endoluminal Grafting for Aneurysmal and Occlusive Disease in the Superficial Femoral Artery: Early Experience, *J. Endovase Surgery*, 2:225–239.

Dorros et al. (1995). "Closure of a Popliteal Arteriovenous Fistula Using an Autologous Vein–Covered Palmaz Stent," *J Endovasc Surgery*, 2:177–181.

Heuser et al. (1995). "Endoluminal Grafting for Percutaneous Aneurysm Exclusion in an Aortocoronary Saphenous Vein Graft: The First Clinical Experience," *J Endovasc Surgery*, 2:81–88.

Hu, T. (1982). "Characterization of the crystallinity of polytetrafluoroethylene by X–ray and IR spectroscopy, differential scanning calorimetry, viscoelastic spectroscopy and the use of a density gradient tube," *Wear*, 82:369–376.

Khanna, Y.P. (1988) "The melting temperature of polytetrafluoroethylene," *Journal of Materials Science Letters*, 7(8):817–818.

Khanna et al. "A New Differential Scanning Calorimetry based Approach for the Estimation of Thermal Conductivity of Polymer solids and Melts," *Polymer Engineering and Science*, 28(16):1034–1041.

Lau et al. (1984). "Glass Transition of Poly(tetrafluoroethylene)," *Macromolecules* 17:1102–1104.

Lau et al. (1984). "The Thermodynamic Properties of Polytetrafluoroethylene," *Journal of Polymer Science: Polymer Physics Edition*, 22:379–405.

Marston et al. (1995). "Transbrachial Endovascular Exclusion of an Axillary Artery Pseudoaneurysm with PTFE––Covered Stents," *J. Endovasc Surgery*, 2:172–176.

Martin, M.L. and Veith, F. J. (1994). "Endoluminal stented graft aorto–bifemoral reconstruction," *Vascular and Endovascular Surgical Techniques*. 3rd Edition, R. M. Greenhalgh ed., W. B. Saunders Company Ltd.: Philadelphia, pp. 100–104.

Martin et al. (1995). "Transluminally placed endovascular stented graft repair for arterial trauma," *The Journal of Vascular Surgery on Compact Disc*, 18(6): 11 unnumbered pages.

May et al. (1995). "Transluminal placement of a prosthetic graft–stent device for treatment of subclavian artery aneurysm," *Journal of Vascular Surgery*, 18(6):10556–1059.

Moore, W. (1994). "Tranfemoral endovascular repair of abdominal aortic aneurysm using the endovascular graft system device,"*Vascular and Endovascular Surgical Techniques*. 3rd Edition, R. M. Greenhalgh ed., W. B. Saunders Company Ltd.: Philadelphia, pp. 78–91.

Palmaz et al. "Uses of balloon expandable stents in combination with PTFE," pp. 36–42.

Palmaz et al. (1995). "Use of Stents Covered With Polytetrafluoroethylene in Experimental Abdinominal Aortic Aneurysm," *Journal of Vascular and Interventional Radiology*, 6(6): 879–885.

Palmaz et al. (1996). "Physical Properties of Polytetrafluoroethylene Bypass Material After Balloon Dilation," *Journal of Vascular and Interventioanl Radiology*, 7(5):657–663.

Papazoglou et al. (1995). "International Congress VIII on Endovascular Interventions" *J Endovasc Surg*, 2:89–129.

Parodi, J. (19910. "Transfemoral intraluminal graft implantation for abdominal aortic aneurysms," *Annals of Vascular Surgery*, 5(6):491–499.

Parodi, J. (1994). "Transfemoral intraluminal graft implantation for abdominal aortic aneurysms," *Vascular and Endovascular Surgical Techniques*.3rd Edition, R. M. Greenhalgh ed., W. B. Saunders Company Ltd.: Philadelphia, pp. 71–77.

Shapiro, M. and Levin, D. (Jun. 1993) "Percutaneous Femoropopliteal Graft Placement: Is This the Next Step?" *Radiology* 187(30: 618–619.

Starkweather, H. W. Jr. (1982). "The Density of Amorphous Polytetrafluoroethylene," *Journal of Polymer Science: Polymer Physics Editions*, 20:2159–2161.

Villani, V. (1990)."A Study on the Thermal Behaviour and Structural Characteristics of Polytetrafluoroethylene," *Thermochimica Acta*, 162:189–193.

"Use of Stents Covered With Polytetrafluoroethylene in Experimental Aortic Aneurysm[1]", *Journal of Vascular and Interventional Radiology* Julio C. Palmaz, M.D., et al.,. vol. 6, No. 6, Nov.–Dec. 1995, pp. 879–885.

"Physical Properties of Polytetrafluoroethylene Bypass Material After Balloon Dilation[1]", *Journal of Vascular and Interventional Radiology* Julio C. Palmaz, M.D., et al., vol 7, No. 5, Sep.–Oct. 1996, pp. 657–663.

"Cardiovascular Implants—Vascular Prostheses", *American National Standard/Association for the Advancement of Medical Instrumentation*, 1994.

"Transfemoral endovascular repair of abdominal aortic aneurysm using the endovascular graft system device", *Vascular and Endovascular Surgical Techniques*, An Atlas, Wesley S. Moore, M.D., 3$^{rd}$ Ed.., 1994, pp. 78–91.

"Endoluminal stented graft aorto–bifemoral reconstruction", *Vascular and Endovascular Surgical Techniques*, An Atlas, Michael L. Marin, M.D. and Frank J. Veith, M.D., 3$^{rd}$ Ed., 1994, pp. 92–99.

"Bifurcated endovascular graft insertion for abdominal aortic aneurysm", Tim Chutter, 1994, pp. 92–99.

"The melting temperature of polytetrafluoroethylene", *Corporate Technology*, Y.P. Khanna, pp. 817–818.

"Macromolecules", *American Chemical Society*, vol. 17, No. 5, 1984, pp. 1102–1104.

"The Density of Amorphous Polytetrafluoroethyylene", *Journal of Polymer Science*, Polymer Physics Edition, vol. 20, 1982, pp. 2159–2161.

"A New Different Scanning Calorimetry Based Approach for the Estimation of Thermal Conductivity of Polymer Solids and Melts", *Polymer Engineering and Science*, Y.P. Khanna, et al., vol. 28, No. 15, Aug. 1988, pp. 1034–1041.

"The Thermodynamic Properties of Polytetrafluoroethylene", *Journal of Polymer Science*, Suk Fai Lau, et al., vol. 22, 1984, pp. 379–405.

"A Study on the Thermal Behaviour and Structural Characteristics of Polytetrafluoroethylene", *Thermochimica Acta*, Vincenzo Villani, vol. 162, 1990, pp. 189–193.

"A Study on the Thermal Behaviour and Structural Characteristics of Polytetrafluoroethylene", *Thermochimica Acta*, Vincenzo Villani, vol. 162, 1990, pp. 189–193.

"Use of Stents Covered With Polytetrafluroethylene in Experimental Abdominal Aortic Aneurysm[1]", *Journal of Vascular and Interventional Radiology*, Julio C. Palmaz, M.D., et al. vol. 6, No. 6, Nov.–Dec. 1995, pp. 879–885.

"Characterization of the crystallinity of polytetrafluoroethylene by X–ray and IR spectroscopy, differential scanning calorimetry, viscoelastic spectroscopy and the use of a density gradient tube", *Department of Mechanical Engineering*, Ting–Yung Hu, vol. 82, 1982, pp. 369–376.

"Endoluminal Grafting: The Arizona Heart Institute Experience", *International Congress VIII on Endovascular Interventions*, SC. Papazoglou, et al. vol. 2, 1995, pp. 89–129.

"Endoluminal Grafting for Percutaneous Aneurysm Exclusion in an Aortocoronary Saphenous Vein Graft: The First Clinical Experience", *J Endovasc Surg*, Richard R. Heuser, M.D., et al.,vol. 2, 1995, pp. 81–88.

"Closure of a Popliteal Arteriovenous Fistula Using an Autologous Vein–Covered Palmaz Stent", *j Endovasc Surg*, Gerald Dorros, M.D., vol. 2, 1995, pp. 177–181.

"Transbrachial Endovascular Exclusion of an Axillary Artery Pseudoaneurysm with PTFE–Covered Stents", *J Endovasc Surg*, William A. Marston, M.D., vol. 2, 1995, pp. 172–176.

"Transbrachial Endovascular Exclusion of an Axillary Artery Pseudoaneurysm with PTFE–Covered Stents", *J. Endovasc Surgery*, William A. Marston, M.D., Vol 2, 1995, pp. 172–176.

"Endoluminal Grafting for Aneurysmal and Occlusive Disease in the Superficial Femoral Artery: Early Experience",*J. Endovase surgery, Endovase Surgery*, Edward B. Dietrich, M.D., vol. 2, 1995, pp. 225–239.

"Transluminally placed endovascular stented graft repair for arterial trauma", *The Journal of Vascular Surgery*, Michael L. Martin, M.D., vol. 18, No. 6, 1995, (11 unnumbered pages).

"Transluminal placement of a prosthetic graft–stent device for treatment o subclavian artery aneurysm", *Journal of Vascular Surgery*, James May, MS, FRACS, FACS, vol. 18, No. 6, 1995, pp. 1056–1059.

"Uses of balloon expandable stents in combination with PTFE", Julio C. Palmaz, M.D., pp. 36–42.

"Transfemoral intraluminal graft implantation for abdominal aortic aneurysms", *Transfemoral intraluminal graft*, Juan C. Parodi, M.D., pp. 71–77.

"Transfemoral endovascular repair of abdominal aortic aneurysm using the endovascular graft system device", *Vascular ad Endovascular Surgical Techniques, Wesley S. Moore, M.D., 3$^{rd}$ Edition*, pp. 78–91.

"Percutaneous Femoropopliteal Graft Placement[1]", *Interventional Radiology*, Andrew H. Cragg, M.D. vol. 187, No. 3, Jun. 1993, pp. 643–648.

"Percutaneous Femoropopliteal Graft Placement: Is This the Next Step?[1]", *Interventional Radiology*, Marcelle J. Shapiro, M.D., et al., vol. 187, No. 3, pp. 618–619.

"Transfemoral Intraluminal Graft Implantation for Abdominal Aortic Aneurysms", *Annals of Vascular Surgery*, J.C. Parodi, M.D., pp. 491–499.

* cited by examiner

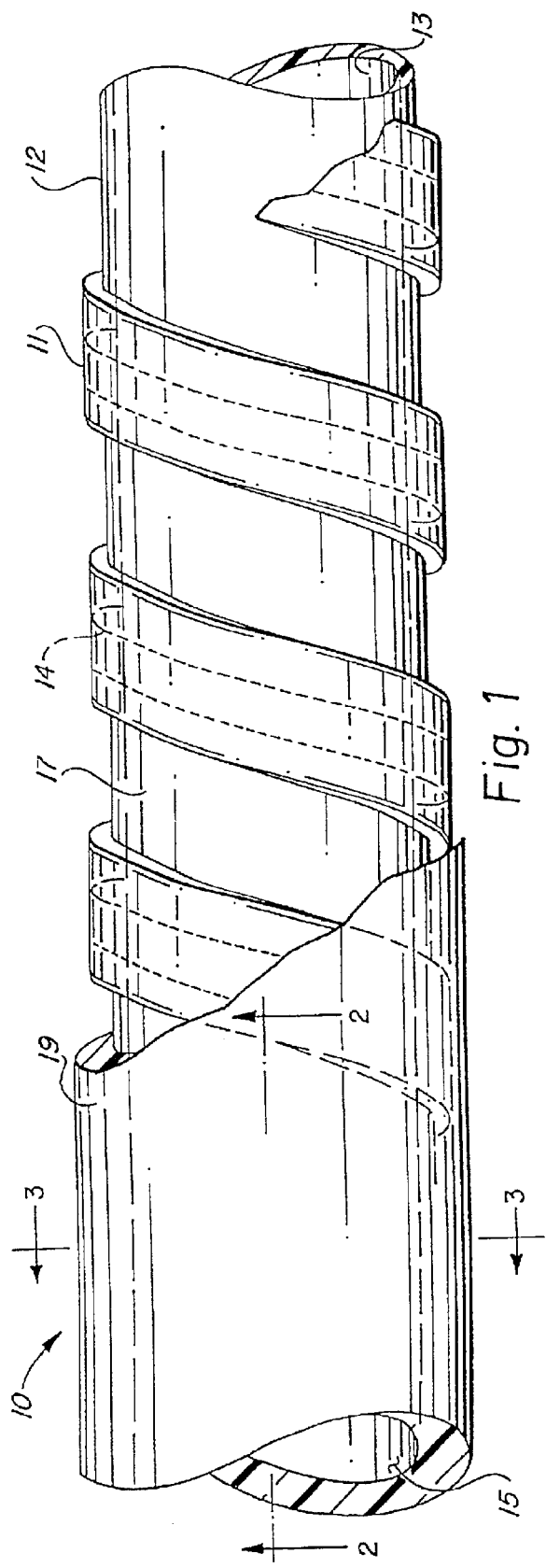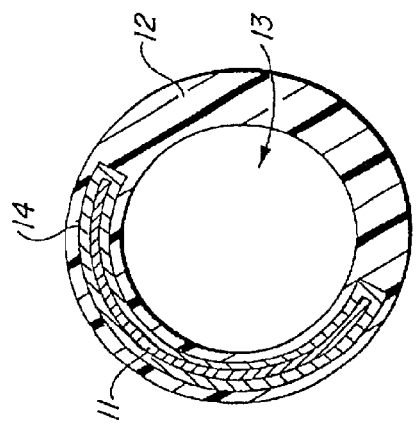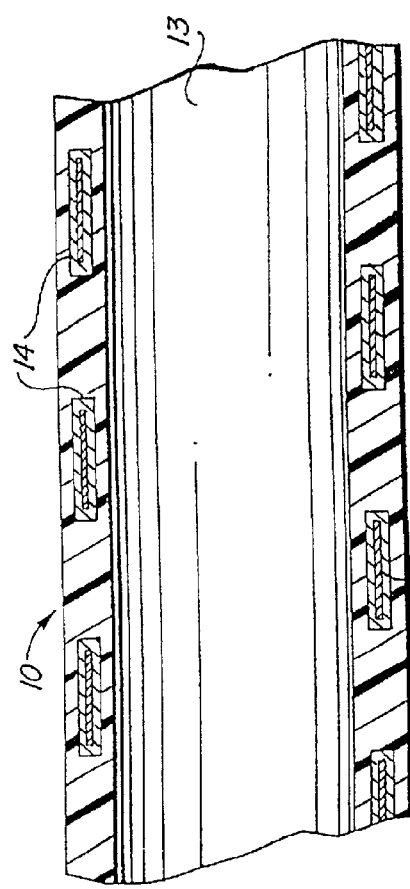

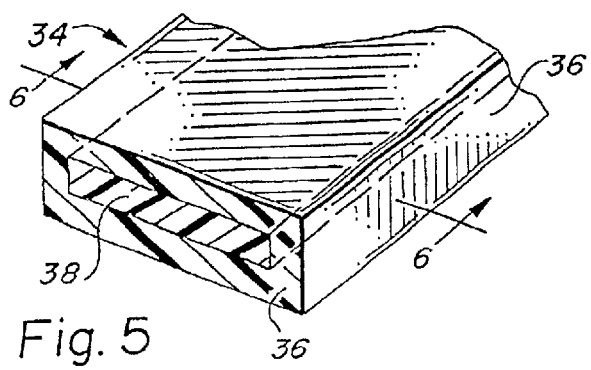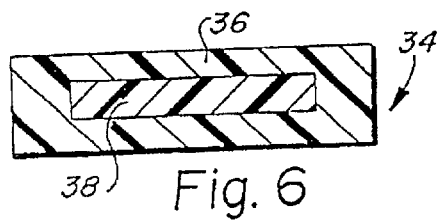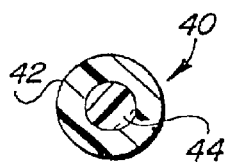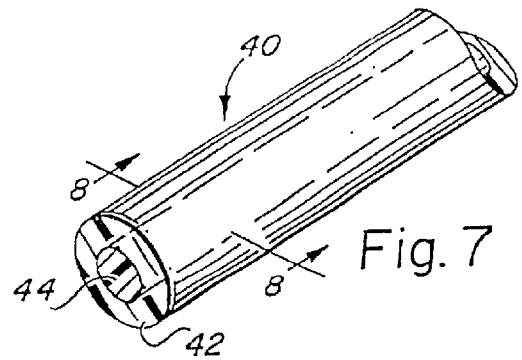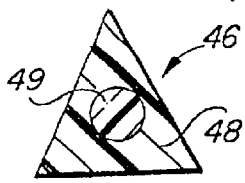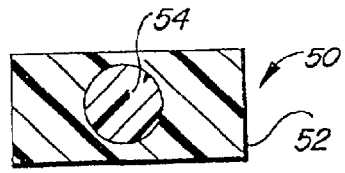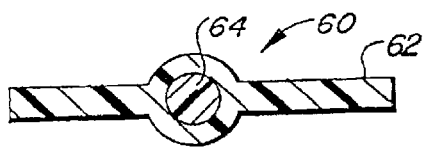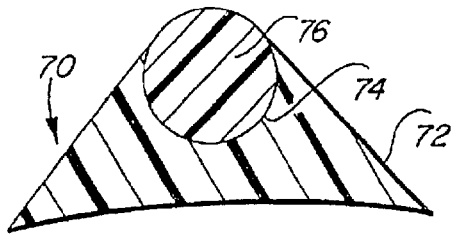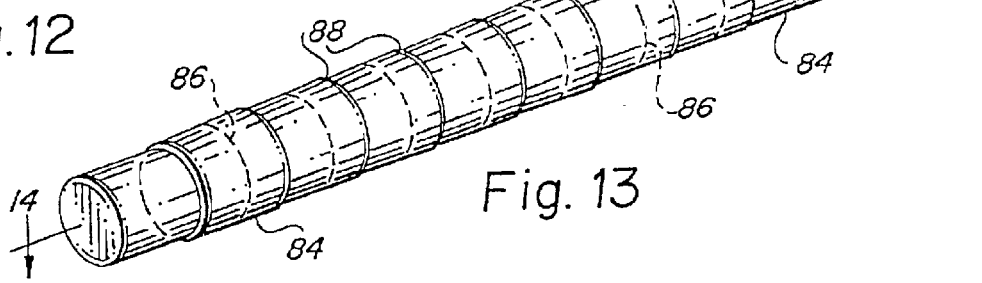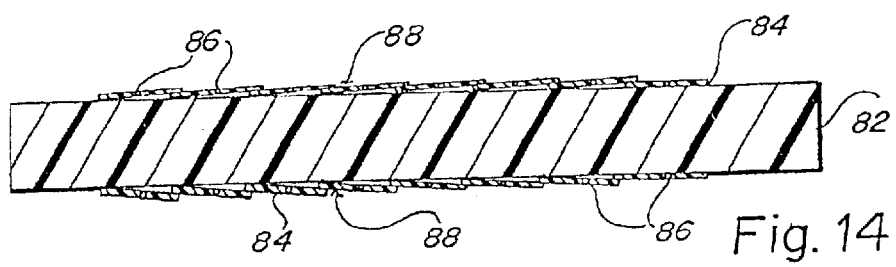

ENDOLUMINAL PROSTHESIS WITH SUPPORT WIRE

CROSS-REFERENCE TO RELATED APPLICATIONS

This application is a divisional of application Ser. No. 09/855,918 filed May 15, 2001, which is a divisional of application Ser. No. 08/999,583, filed Dec. 22, 1997, now U.S. Pat. No. 6,264,684, which is a continuation-in-part of three applications: 1) International Application No. PCT/US95/16497, filed Dec. 8, 1995, which was nationalized as Ser. No. 09/077,533, filed May 28, 1998, now U.S. Pat. No. 6,053,943; 2) Ser. No. 08/833,797, filed Apr. 9, 1997, now U.S. Pat. No. 6,451,047, which is a continuation-in-part of application Ser. No. 08/508,033, filed Jul. 27, 1995, now U.S. Pat. No. 5,749,880, which is a continuation-in-part of application Ser. No. 08/401,871, filed Mar. 10, 1995, now U.S. Pat. No. 6,124,523; and 3) which is a continuation-in-part of Ser. No. 08/794,871, filed Feb. 5, 1997, now U.S. Pat. No. 6,039,755. This application expressly incorporates by reference the entirety of each of the above-mentioned applications as if fully set forth herein.

BACKGROUND OF THE INVENTION

Most intraluminal stents are formed of an open lattice fashioned either to be elastically deformable, such as in the case of self-expanding stainless steel spring stents, plastically deformable, such as in the case of balloon-expandable stainless steel PALMAZ stents, or thermally expandable such as by employing shape memory properties of the material used to form the stent. A common problem of most conventional intraluminal stents is re-occlusion of the vessel after stent placement. Tissue ingrowth and neointimal hyperplasia significantly reduces the open diameter of the treated lumen over time, requiring additional therapies.

The present invention makes advantageous use of the known biocompatible and material properties of ePTFE vascular grafts, and adds an abluminal supporting structure capable of being diametrically reduced to an intraluminal delivery profile and self-expanding in vivo to conform to the anatomical topography at the site of intraluminal implantation. More particularly, the present invention consists of an ePTFE substrate material, such as that described in U.S. application Ser. No. 08/794,871, filed Feb. 5, 1997, now U.S. Pat. No. 6,039,755, as a carrier for a helically wound, open cylindrical support structure made of a shape memory alloy.

The inventive intraluminal stent-graft device may be implanted either by percutaneous delivery using an appropriate delivery system, a cut-down procedure in which a surgical incision is made and the intraluminal device implanted through the surgical incision, or by laparoscopic or endoscopic delivery.

Shape memory alloys are a group of metal alloys which are characterized by an ability to return to a defined shape or size when subjected to certain thermal or stress conditions. Shape memory alloys are generally capable of being plastically deformed at a relatively low temperature and, upon exposure to a relatively higher temperature, return to the defined shape or size prior to the deformation. Shape memory alloys may be further defined as one that yields a thermoelastic martensite. A shape memory alloy which yields a thermoelastic martensite undergoes a martensitic transformation of a type that permits the alloy to be deformed by a twinning mechanism below the martensitic transformation temperature. The deformation is then reversed when the twinned structure reverts upon heating to the parent austenite phase. The austenite phase occurs when the material is at a low strain state and occurs at a given temperature. The martensite phase may be either temperature induced martensite (TIM) or stress-induced martensite (SIM). When a shape memory material is stressed at a temperature above the start of martensite formation, denoted $M_s$, where the austenitic state is initially stable, but below the maximum temperature at which martensite formation can occur, denoted $M_d$, the material first deforms elastically and when a critical stress is reached, it begins to transform by the formation of stress-induced martensite. Depending upon whether the temperature is above or below the start of austenite formation, denoted $A_s$, the behavior when the deforming stress is released differs. If the temperature is below $A_s$, the stress-induced martensite is stable, however, if the temperature is above $A_s$, the martensite is unstable and transforms back to austenite, with the sample returning to its original shape. U.S. Pat. Nos. 5,597,378, 5,067,957 and 4,665,906 disclose devices, including endoluminal stents, which are delivered in the stress-induced martensite phase of shape memory alloy and return to their pre-programmed shape by removal of the stress and transformation from stress-induced martensite to austenite.

Shape memory characteristics may be imparted to a shape memory alloy by heating the metal at a temperature above which the transformation from the martensite phase to the austenite phase is complete, i.e., a temperature above which the austenite phase is stable. The shape imparted to the metal during this heat treatment is the shape "remembered." The heat treated metal is cooled to a temperature at which the martensite phase is stable, causing the austenite phase to transform to the martensite phase. The metal in the martensite phase is then plastically deformed, e.g., to facilitate its delivery into a patient's body. Subsequent heating of the deformed martensite phase to a temperature above the martensite to austenite transformation temperature, e.g., body temperature, causes the deformed martensite phase to transform to the austenite phase and during this phase transformation the metal reverts back to its original shape.

The term "shape memory" is used in the art to describe the property of an elastic material to recover a pre-programmed shape after deformation of a shape memory alloy in its martensitic phase and exposing the alloy to a temperature excursion through its austenite transformation temperature, at which temperature the alloy begins to revert to the austenite phase and recover its preprogrammed shape. The term "pseudoelasticity" is used to describe a property of shape memory alloys where the alloy is stressed at a temperature above the transformation temperature of the alloy and stress-induced martensite is formed above the normal martensite formation temperature. Because it has been formed above its normal temperature, stress-induced martensite reverts immediately to undeformed austenite as soon as the stress is removed provided the temperature remains above the transformation temperature.

The present invention employs a wire member made of either a shape memory alloy, preferably a nickel-titanium alloy known as NITINOL, spring metal allays such as spring stainless steel or other elastic metal or plastic alloys, or composite material, such as carbon fiber. It is preferable that the wire member have either a generally circular, semi-circular, triangular or quadrilateral transverse cross-sectional profile. Where a shape memory alloy material is employed, pre-programmed shape memory is imparted to the wire member by helically winding the wire member about a cylindrical programming mandrel having an outer diametric dimension substantially the same, preferably within a tolerance of about +0 to −15%, as the ePTFE substrate and annealing the programming mandrel and the wire member at a temperature and for a time sufficient to impart the desired shape memory to the wire member. After annealing, the wire member is removed from the programming mandrel, straightened and helically wound about the abluminal wall surface of an ePTFE tubular member at a temperature below the $A_s$ of the shape memory alloy used to form the wire member.

In order to facilitate bonding of the wire member to the ePTFE tubular member, it is preferable that a bonding agent capable of bonding the support wire member to the ePTFE tubular member be used at the interface between the wire member and the ePTFE tubular member. Suitable biocompatible bonding agents may be selected from the group consisting of polytetrafluoroethylene, polyurethane, polyethylene, polypropylene, polyamides, polyimides, polyesters, polypropylenes, polyethylenes, polyfluoroethylenes, silicone fluorinated polyolefins, fluorinated ethylene/propylene copolymer, perfluoroalkoxy fluorocarbon, ethylene/tetrafluoroethylene copolymer, and polyvinylpyrolidone. The bonding agent may constitute an interfacial layer intermediate the wire member and the ePTFE tubular member, or may be a polymeric cladding at least partially concentrically surrounding the wire member. Where a cladding is provided, the cladding is preferably a polymeric material selected from the group consisting of polytetrafluoroethylene, polyurethane, polyethylene, polypropylene, polyamides, polyimides, polyesters, polypropylenes, polyethylenes, polyfluoroethylenes, silicone fluorinated polyolefins, fluorinated ethylene/propylene copolymer, perfluoroalkoxy fluorocarbon, ethylene/ tetrafluoroethylene copolymer, and polyvinylpyrolidone. The cladding may be either co-extruded with the wire member, extruded as a tube into which the wire member is concentrically inserted after annealing the wire member, or provided as an elongate member which a longitudinal recess which co-axially receives the wire member. Where the bonding agent employed is a melt thermoplastic which has a melt point below the crystalline melt point of polytetrafluoroethylene, the melt thermoplastic bonding agent and the wire member are wound about the ePTFE tubular member, and constrained thereupon, such as by application of circumferential pressure, then the assembly is then exposed to the melt temperatures without longitudinally supporting the assembly. However, where the bonding agent is polytetrafluoroethylene, bonding of the wire member to the ePTFE tubular member requires exposing the assembly to temperatures above the crystalline melt point of polytetrafluoroethylene in order to effectuate bonding of the wire member to the ePTFE. This is preferably accomplished by introducing the assembly into a sintering oven while the assembly is on a mandrel and the assembly secured to the mandrel by an external helical wrapping of TEFLON tape applied to opposing ends of the assembly to longitudinally constrain the assembly and reduce or eliminate the tendency of the assembly to longitudinally foreshorten during sintering.

SUMMARY OF THE INVENTION

It is a primary objective of the present invention to provide a self-supporting, self-expanding stent-graft device which is capable of being delivered to an anatomical position within a human body in a first constrained configuration, positioned in vivo at a desired anatomical site, and the constraint released to permit the stent-graft device to transform to a radially enlarged second configuration.

It is another primary objective of the present invention to provide a stent-graft device which consists generally of tubular member fabricated of a biocompatible polymer selected from the group of microporous expanded polytetrafluoroethylene ("ePTFE"), polyethylene, polyethylene terepthalate, polyurethane and collagen, and at least one winding of a elastically self-expanding wire coupled to either the abluminal or luminal surfaces of the ePTFE tubular member or interdisposed between concentrically positioned ePTFE tubular members.

It is a further objective of the present invention to couple the at least one winding of the elastically self-expanding wire to the ePTFE tubular member by cladding a support wire in a polymeric material which has a melt point less than or equal to that of the ePTFE tubular member and below the $A_s$ temperature of the shape memory alloy metal wire.

It is a further objective of the present invention to provide an adhesive interlayer for bonding the shape memory alloy metal wire to the tubular member, the adhesive interlayer being selected from the group consisting of polytetrafluoroethylene, polyurethane, polyethylene, polypropylene, polyamides, polyimides, polyesters, polypropylenes, polyethylenes, polyfluoroethylenes, silicone, fluorinated polyolefins, fluorinated ethylene/ propylene copolymer, perfluoroalkoxy fluorocarbon, ethylene/tetrafluoroethylene copolymer, and polyvinylpyrolidone.

It is another objective of the present invention to provide a method for making a self-expanding stent-graft device comprised generally of an ePTFE tubular member and at least one winding of a shape memory alloy metal wire coupled to the abluminal surface of the ePTFE tubular member.

These and other objects, features and advantages of the present invention will be better understood by those of ordinary skill in the art from the following more detailed description of the present invention taken with reference to the accompanying drawings and its preferred embodiments.

BRIEF DESCRIPTION OF THE DRAWINGS

FIG. 1 is a side elevational view of a supported intraluminal graft in accordance with a preferred embodiment of the present invention.

FIG. 2 is a cross-sectional view taken along line 2—2 of FIG. 1.

FIG. 3 is a cross-sectional view taken along line 3—3 of FIG. 1.

FIG. 5 is a perspective view of a ribbon member clad in a polymeric covering in accordance with the present invention.

FIG. 6 is a cross-sectional view taken along line 6—6 of FIG. 5.

FIG. 7 is a perspective view of a wire member clad in a polymeric covering in accordance with the present invention.

FIG. 8 is a cross-sectional view taken along line 8—8 of FIG. 7.

FIG. 9 is a diagrammatic cross-sectional view of a first embodiment of a support member encapsulated in a shaped polymeric cladding covering.

FIG. 10 is a diagrammatic cross-sectional view of a second embodiment of a support member encapsulated in a shaped polymeric cladding covering.

FIG. 11 is a diagrammatic cross-sectional view of a third embodiment of a support member encapsulated in a shaped polymeric cladding covering.

FIG. 12 is a diagrammatic cross-sectional view of a fourth embodiment of a support member coupled to a shaped polymeric cladding covering.

FIG. 13 is a perspective view of an alternative preferred embodiment of the supported intraluminal graft in accordance with the present invention.

FIG. 14 is a cross-sectional view taken along line 14—14 of FIG. 13.

DETAILED DESCRIPTION OF THE PREFERRED EMBODIMENTS

Figure 4A:
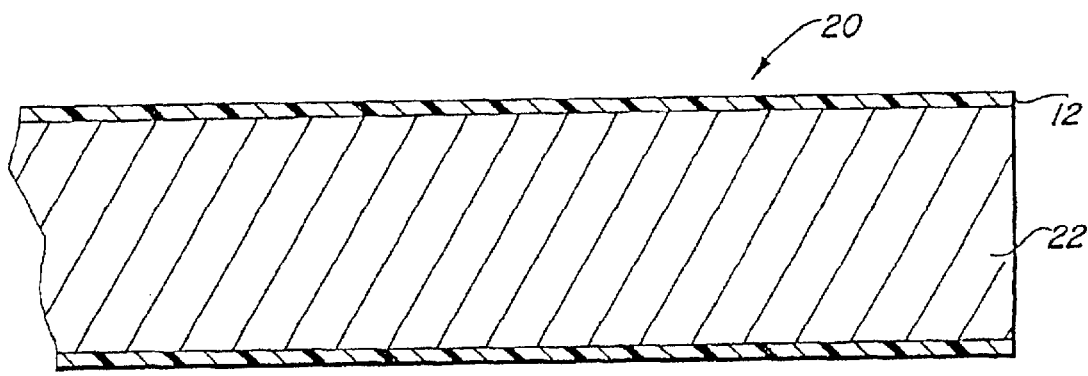
FIG. 4A is a side elevational cross-sectional view of a graft member mounted onto a mandrel in accordance with a preferred embodiment of the method of the present invention.

The shape memory alloy supported intraluminal graft 10 of the present invention consists generally of a tubular substrate 12 having a central lumen 13 passing through an entire longitudinal extent of the tubular substrate. The tubular substrate 12 has a luminal wall surface 15 adjacent the central lumen 13 and an abluminal wall surface 17 opposing the central lumen 13. A support member 14 is provided and is preferably at least partially covered by a polymeric cladding 11. The polymeric clad support member 14 is circumferentially disposed about and joined to the abluminal wall surface 17 of the tubular substrate 12, such as by helically winding the polymeric clad support member 14 about the abluminal surface 17 of the tubular substrate 12. Optionally, a second tubular substrate 19, having an inner diameter sufficiently dimensioned to be concentrically engaged about the abluminal wall surface 17 of the tubular substrate 12 and the polymeric clad support member 14, may be provided.

In accordance with a first preferred embodiment of the present invention, and with particular reference to FIGS. 1–3, there is provided the inventive supported intraluminal graft 10 comprised of a tubular 12 made of a biocompatible polymeric material, such as expanded polytetrafluoroethylene ("ePTFE"), polyethylene terepthalate ("PET") such as that marketed and sold under the trademark DACRON, polyethylene, or polyurethane. Expanded PTFE substrate materials are preferably made by ram extruding an admixture of polytetrafluoroethylene resin and a hydrocarbon lubricant to form a tubular extrudate, drying off the hydrocarbon lubricant, longitudinally expanding the dried tubular extrudate, then sintering the longitudinally expanded dried tubular extrudate at a temperature above the crystalline melt point of polytetrafluoroethylene. The resulting tubular ePTFE material has a microporous microstructure which is composed of spaced-apart nodes interconnected by fibrils, with the fibrils being oriented parallel to the longitudinal axis of the ePTFE tube and parallel to the axis of longitudinal expansion. U.S. Pat. Nos. '390 and '566, both issued to Gore, teach processes for making ePTFE tubular substrates and are hereby incorporated by reference as teaching processes to make ePTFE tubular and planar materials. A tubular substrate may also be made by weaving yarn, made of either polyester or ePTFE, into a tubular structure as is well known in the art. Additionally, the tubular substrate 12 may have a cylindrical profile having a substantially uniform internal diameter along its longitudinal axis, or may have a tapered sidewall in which the tubular substrate 12 assumes a generally frustroconical shape in which the internal diameter of the tubular substrate 12 increases or deceases along the longitudinal axis of the tubular substrate 12. Alternatively, the tubular substrate 12 may have at least one region of stepped diameter in which the internal diameter of the tubular substrate changes at a discrete longitudinal section of the tubular substrate 12.

In accordance with a first preferred embodiment of the present invention, the tubular substrate 12 is an extruded, longitudinally expanded and sintered ePTFE tubular member which has been radially expanded from an initial luminal inner diameter of between about 1.5 mm to about 6 mm to a final luminal inner diameter of between about 3 mm to about 18 mm. Thus, tubular substrate 12 is initially fabricated at a first relatively smaller diametric dimension, dried of the hydrocarbon lubricant, and sintered, then radially expanded by application of an radially outwardly directed force applied to the luminal wall surface 15 of the tubular substrate 12, which radially deforms the wall of the tubular substrate 12 from an initial luminal inner diameter, denoted $D_1$, to a second, enlarged luminal inner diameter, denoted $D_2$. Alternatively, tubular substrate 12 may be provided as an extruded, longitudinally expanded and sintered ePTFE tubular member having an inner diameter equivalent to the final inner diameter of the supported intraluminal graft, e.g., extruded to a luminal diameter of between about 3 mm to about 18 mm, and a wall thickness sufficient to acceptably minimize the delivery profile of the supported intraluminal graft. Suitable wall thicknesses for the non-radially expanded ePTFE tubular member are considered less than or equal to about 0.3 mm for delivery to peripheral anatomic passageways.

The tubular substrate 12 is preferably radially expanded by loading the tubular substrate 12, in its fully or partially sintered state, onto an inflation balloon such that the tubular substrate 12 is concentrically engaged upon the inflation balloon, introducing the inflation balloon and tubular substrate 12 into a tubular housing defining a generally cylindrical cavity having an inner diameter corresponding to the maximum desired outer diameter of the final shape memory alloy supported graft, and applying a fluid pressure to the inflation balloon to inflate the inflation balloon and radially deform the tubular substrate 12 into intimate contact with the generally cylindrical cavity. Pressure is maintained within the inflation balloon for a period of time sufficient to minimize the inherent recoil property of the ePTFE material in the tubular substrate 12, then the pressure is relieved and the inflation balloon permitted to deflate. The radially deformed tubular substrate, now having an inner luminal diameter $D_2$, is removed from the generally cylindrical cavity for subsequent processing.

During radial expansion of the tubular substrate 12 from $D_1$ to $D_2$, the node and fibril microstructure of the ePTFE tubular substrate is deformed. The nodes, which have an orientation perpendicular to the longitudinal axis of the tubular substrate 12 and parallel to the radial axis of the tubular substrate 12, deform along the longitudinal axis of each node to form elongated columnar structures, while the length of the fibrils interconnecting adjacent pairs of nodes in the longitudinal axis of the tubular substrate 12, remains substantially constant. The fibril length is also referred to herein as the "internodal distance."

A support member 14, which is preferably made of an elastic wire material selected from the group of thermoelastic or shape memory alloys, spring stainless steel, elastic metal or plastic alloys, or composite materials, such as woven carbon fibers. Where a shape memory alloy is employed, it is important that the shape memory alloy have a transition temperature below human body temperature, i.e., 37 degrees Celsius, to enable the shape memory alloy to undergo transformation to the austenite phase when the shape memory alloy wire member is exposed to human body temperature in vivo. In accordance with the best mode currently known for the present invention, the preferred shape memory alloy is a near equiatomic alloy of nickel and titanium.

To facilitate attachment of the elastic or thermoelastic wire member 14 to the tubular substrate 12, it is contemplated that a polymeric cladding 11 be provided to at least partially cover the support wire member 14 and facilitate adhesion between the support wire member 14 and the abluminal wall surface 17 of the tubular substrate 12. In accordance with the best mode for practicing the present invention, it is preferable that the polymeric cladding 11 be selected from the group of biocompatible polymeric materials consisting of polytetrafluoroethylene, polyurethane, polyethylene, polypropylene, polyamides, polyimides, polyesters, polypropylenes, polyethylenes, polyfluoroethylenes, silicone, fluorinated polyolefins, fluorinated ethylene/propylene copolymer, perfluoroalkoxy fluorocarbon, ethylene/tetrafluoroethylene copolymer, and polyvinylpyrolidone. As will hereinafter be described more fully, the polymeric cladding 11 may be coupled to the support wire member 14 by any of a variety of known methodologies. For example, the polymeric cladding 11 may be co-extruded with the support wire member 14, the polymeric cladding 11 may be extruded with an opening passing through the polymeric cladding 11 along its longitudinal axis and dimensioned to receive the support wire member 14 there through, the polymeric cladding 11 may have a longitudinally extending recess dimensioned to receive and retain the support wire member 14 therein, or the polymeric cladding 11 may be applied onto the support wire member 11 in dispersion form, such as by dip-coating or spraying, and the solvent or aqueous vehicle dried thereby forming a covering on the support wire member 11.

The support wire member 14 in its polymeric cladding 11 is circumferentially joined to the abluminal wall surface 17 of the tubular substrate 12, such as by helically winding at least one length of polymeric clad support wire member 14 in a regular or irregular helical pattern, or by applying the polymeric clad support wire member 14 as a series of spaced-apart circumferential rings, along at least a portion of the longitudinal axis of the abluminal wall surface 17 of the tubular substrate 12. It is preferable that the tubular substrate 12 be mounted onto a supporting mandrel [not shown] having an outer diameter closely toleranced to the inner diameter of the tubular substrate 12 to permit the tubular substrate 12 to be placed thereupon and secured thereto without deforming the tubular substrate 12.

A second tubular member 19 may, optionally, be concentrically engaged about the tubular member 12 and the polymeric clad support wire member 14. As more clearly depicted in FIGS. 2–3, where the second tubular member 19 is employed and disposed circumferentially about the tubular member 12 and the polymeric clad support wire member 14, the tubular member 12 and the second tubular member 19 encapsulate the polymeric clad support wire member 14. Where the tubular member 12 and the second tubular member 19 are both made of longitudinally expanded ePTFE, each will have a microporous microstructure in which the fibrils are oriented parallel to the longitudinal axis of each of the tubular member 12 and the second tubular member 19, throughout their respective wall thicknesses. The encapsulation of the polymeric clad support wire member 14 is best accomplished by providing both the tubular member 12 and the second tubular member 19 as unsintered or partially sintered tubes. After wrapping the polymeric clad support wire member 14 about the abluminal surface of the tubular member 12, and circumferentially engaging the second tubular member 19 thereabout, it is preferable to apply a circumferential pressure to the assembly, while the assembly is on the supporting mandrel [not shown]. Circumferential pressure may be applied to the assembly by, for example, helically wrapping tetrafluoroethylene film tape about the abluminal surface of the second tubular member 19 along its longitudinal axis, or by securing opposing ends of the assembly on the supporting mandrel, and rolling the assembly to calendar the assembly. After the circumferential pressure is applied to the assembly, the assembly is then introduced into either a convention or radiant heating oven, set at a temperature above the melt point of the material used to fabricate the tubular member 12, the second tubular member 19 and/or the polymeric cladding 11, for a period of time sufficient to bond the tubular member 12, the second tubular member 19 and the polymeric cladding 11 into a substantially monolithic, unitary structure. Where polytetrafluoroethylene is used, it has been found that it is preferable to heat the assembly in a radiant heating oven.

Figure 4B:
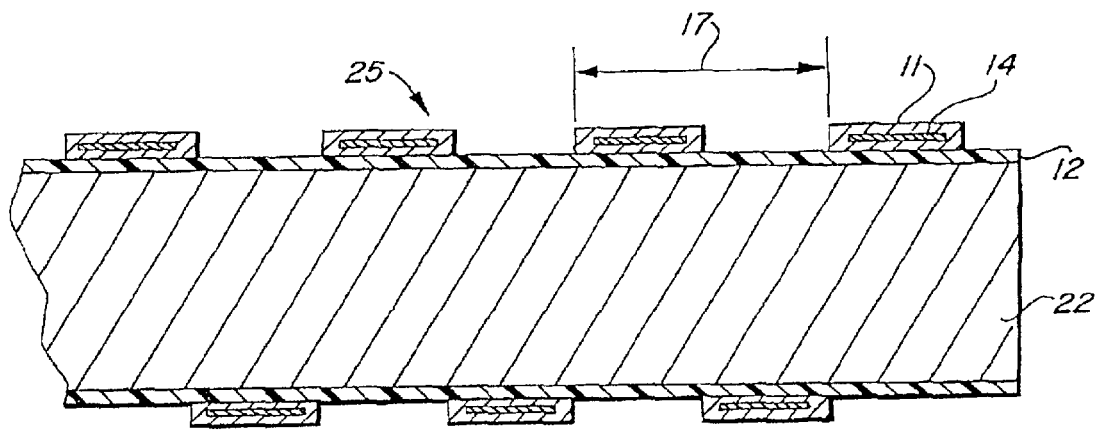
FIG. 4B is a side elevational cross-sectional view of FIG. 4A with a support member wrapped about an abluminal surface of the graft member.
Figure 4C:
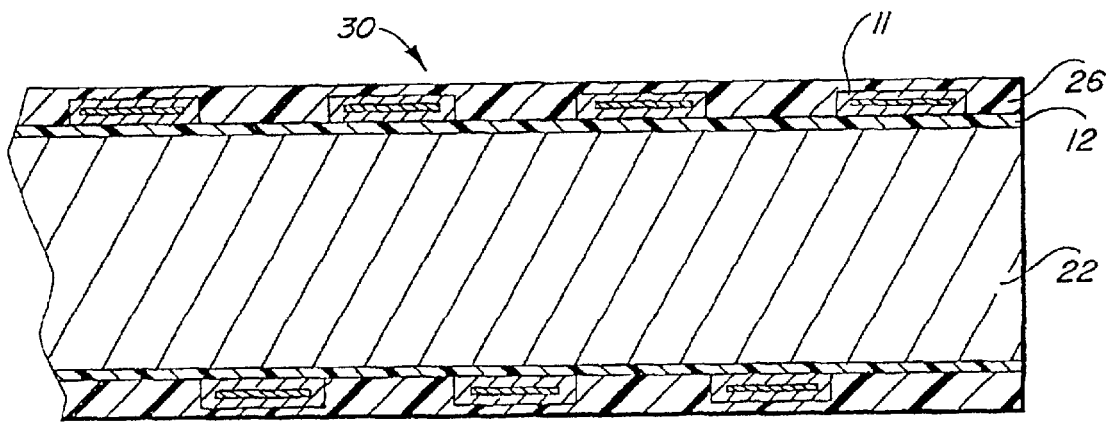
FIG. 4C is a side elevational cross-sectional view as in FIGS. 4A and 4B illustrating an abluminal covering concentrically superimposed over they support member and the graft member.

FIGS. 4A–4C depict the method steps for making the inventive shape memory alloy supported intraluminal graft 10. With a first step 20, tubular member 12 is concentrically engaged onto a supporting mandrel 22 such that the supporting mandrel 22 resides within the lumen of the tubular member 12. A helical winding of polymeric clad support wire member 14 is applied about the abluminal wall surface 17 of the tubular member 12 at step 25. The helical windings have an interwinding distance 27 which is preferably at least one times the distance 29 which represents the width of the polymer cladding 11, in the case of a planar polymer cladding 11, or the diameter, in the case of a tubular polymer cladding 11 having a circular transverse cross-section. The helical winding of the polymeric clad support wire member 14 contacts the abluminal wall surface 17 of the tubular member 12 at an interfacial region 28. According to one preferred embodiment of the present invention there is provided an adhesive material 23 selected from the group consisting of polytetrafluoroethylene, polyurethane, polyethylene, polypropylene, polyamides, polyimides, polyesters, polypropylenes, polyethylenes, polyfluoroethylenes, silicone, fluorinated polyolefins, fluorinated ethylene/propylene copolymer, perfluoroalkoxy fluorocarbon, ethylene/tetrafluoroethylene copolymer, and polyvinylpyrolidone. The adhesive material is preferably applied to the interfacial region 28 of the polymeric clad support wire member 14, but may also be applied in a pattern directly to a surface of the tubular substrate and the SMA wire member 14 brought into contact with the adhesive material. In this manner, as the polymeric clad support wire member 28 is helically applied to the abluminal wall surface 17 of the tubular member 12, the adhesive material 23 forms an interlayer intermediate the polymeric clad support wire member 28 and the abluminal wall surface 17 of the tubular member 12.

Where the selected adhesive material 23 has a melt point less than the crystalline melt point of polytetrafluoroethylene, i.e., about 327 degrees Centigrade, the resulting assembly of step 25 may be introduced into a heating oven set at the melt temperature of the selected adhesive material 23, for a period of time sufficient to melt the adhesive material 23 and impart an adhesive bond between the polymeric clad support wire member 14 and the tubular member 12. On the other hand, where the selected adhesive material 23 is polytetrafluoroethylene, an external covering of a second tubular member 26 may be concentrically engaged about the assembly resulting from step 25, a circumferential pressure exerted to the second tubular member 26, thereby bringing the second tubular member 26, the polymer clad support wire member 11 and the tubular member 12 into intimate contact with one another, and the entire assembly introduced into a sintering oven set at a temperature above the crystalline melt point of polytetrafluoroethylene and for a period of time sufficient to meld the second tubular member 26 and the tubular member 12 to one another to form a resultant substantially monolithic structure which is substantially devoid of interfacial demarcations between the second tubular member 26 and the tubular member 12, with the polymer clad support wire member 14 residing intermediate there between.

Turning now to FIGS. 5–12, there is depicted numerous alternate configurations of the polymer clad support wire member 14. FIGS. 5 and 6 depict a first embodiment of the polymer clad support wire member 34 in which the support wire member is formed as a planar ribbon wire 38 having a generally tubular box-like polymer cladding 36 provided about the outer surfaces of the planar ribbon wire 38. In the transverse cross-sectional view of FIG. 6 it will be seen that both the planar ribbon wire 38 and the polymer cladding 36 have generally quadrilateral cross-sectional configurations.

FIGS. 7–8 depict a second embodiment of the polymer clad support wire member 40 in which the support wire member is formed as a cylindrical wire 44 having a generally tubular polymer cladding 42 provided about the outer circumference of the planar ribbon wire 44. In the transverse cross-sectional view of FIG. 8 it will be seen that both the cylindrical wire 44 and the polymer cladding 42 have generally circular cross-sectional configurations.

FIGS. 9–12 are provided in the transverse cross-sectional views only, it being understood that like FIGS. 5 and 7, each of the embodiments depicted in FIGS. 9–12 have corresponding perspective configurations. FIG. 9 depicts a third embodiment of the polymer clad support wire member 46 in which the support wire member is formed as a cylindrical wire 49 having a generally triangular-shaped polymer cladding 48, with a central longitudinal cylindrical bore to accommodate the cylindrical wire 49 therein, which is provided about the outer surfaces of the cylindrical wire 49. A fourth embodiment of the polymer clad support wire member 50 is depicted in FIG. 10. Polymer clad support wire member 50 consists generally of a polymer cladding 52 having a plurality of planar surfaces and having a generally quadrilateral transverse cross-sectional shape, while the support wire member 54 is generally cylindrical with a generally circular transverse cross-section. As depicted in FIG. 11, a fifth embodiment of the polymer clad support wire member 60 is depicted. Here, the support wire member 54 has a generally cylindrical shape with a generally circular transverse cross-section, while the polymer cladding 62 has a main body portion having a generally circular transverse cross-section, but has additional projections extending radially outward from the generally circular main body portion to increase the bonding surface area of the polymer clad support wire member 60. Finally, as depicted in FIG. 12, the sixth embodiment of the polymer clad support wire member 70 is depicted. In accordance with this sixth embodiment there is provided a generally cylindrical support wire member 76 having a generally circular transverse cross-section, while the polymer cladding 72 is provided with a generally triangular cross-sectional shape, with hemispherical recess 74 formed in an apex of the generally triangular cross-sectional shape. The hemispherical recess 74 subtends at least a 180 degree arc and extends along a substantial longitudinal extent of the polymer cladding 72. The generally cylindrical support wire member 76 is engaged in the hemispherical recess 74 and retained therein by an interference fit, or by other suitable means, such as an adhesive.

It will be understood by those skilled in the art, that each of the foregoing embodiments of the polymer clad support wire member may be made by pulltrusion methods in which the shape memory alloy wire member, having a preprogrammed austenite phase, is fed into an extruder during extrusion of the polymer cladding, or by extruding the polymer cladding with a central lumen, dimensioned appropriately to permit engagement of the shape memory alloy wire, then threading the support wire member into the central lumen of the polymer cladding.

Finally, an alternative embodiment of a shape memory alloy supported intraluminal graft 80 is depicted in FIGS. 13 and 14. The inventive shape memory alloy supported intraluminal graft 80 may be formed by helically wrapping a length of polymer clad 84 shape memory alloy wire 86 about a supporting winding mandrel, such that the polymer cladding 84 has overlapping regions 88 which form seams. The resulting assembly is then heated above the melt point of the polymer cladding 84 to join and seal the overlapping regions 88 to one another.

Figure 15:
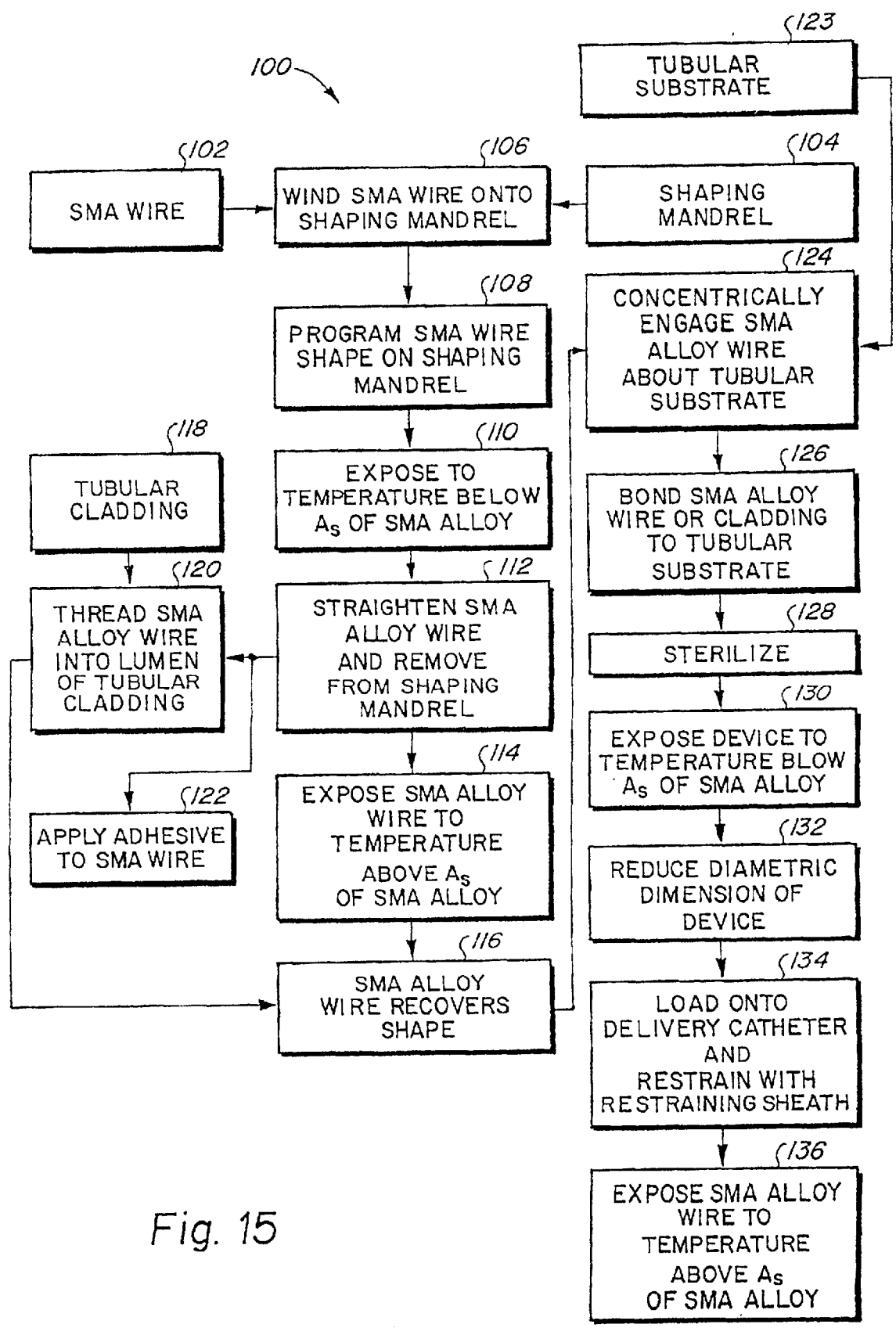
FIG. 15 is a process flow diagram illustrating the process steps for making the supported intraluminal graft in accordance with the method of the present invention.

The inventive method 100 for making the inventive wire supported intraluminal graft, described above, is illustrated with reference to FIG. 15. An elastic or thermoelastic wire member is provided at step 102 along with a shaping mandrel 104. The shaping mandrel 104 is preferably a solid cylindrical or tubular cylindrical stainless steel member capable of withstanding annealing temperatures of shape memory alloys. At step 106, the wire member provided at step 102 is wound onto the shaping mandrel provided at step 104. The wire member is preferably helically wound about the shaping mandrel such that adjacent windings are substantially uniformly spaced from one another. It is also contemplated that the wire member may be wound about the shaping mandrel in any of a wide number of configurations, including non-uniformly spaced windings long portions of the shaping mandrel, such that certain regions of the winding have higher and lower frequency windings than other regions, that the winding be shaped as adjacent circumferential loops such as that shape disclosed in Gianturco, U.S. Pat. No. 4,907,336 or Wiktor, U.S. Pat. No. 4,969,458, both hereby incorporated by reference as teaching a shape of winding suitable for use with the present invention, or virtually any other shape which is capable for forming an open tubular structural skeleton, including, without limitation, a helical winding having a plurality of sinusoidal bends along a length thereof, as taught by Wiktor, U.S. Pat. No. 4,886,062 or Pinchuck, U.S. Pat. No. 5,019,090, both hereby incorporated by reference as teaching alternative configurations of helical windings of wire members.

Where a thermoelastic shape memory alloy (SMA) wire member is utilized, the SMA wire member is wound about the shaping mandrel, the shape of the wound SMA wire member is programmed at step 108 by annealing the SMA wire member at a temperature and for a time sufficient to impart shape memory properties to the SMA wire member. At step 110, the preprogrammed SMA alloy wire member is then exposed to temperature conditions below the $M_f$ temperature of the SMA alloy. While it is maintained below the $M_f$ temperature of the SMA alloy, the wire member is removed from the shaping mandrel and straightened to a linear shape at step 112. If the SMA alloy wire member is to be covered with a cladding, a polymeric tubular cladding is provided at step 118 and the SMA alloy wire member is threaded into the lumen of the tubular cladding at step 120. It is preferable that steps 118 and 120 be performed while the SMA alloy wire member is maintained at a temperature below the $M_f$ temperature of the SMA alloy to prevent shape recovery of the SMA alloy wire member. Alternatively, if no polymeric cladding is to be employed, but the SMA alloy wire member from step 112 is to be adhered, an adhesive material may be applied to the SMA alloy wire member at step 122. Step 122 may be conducted while the SMA alloy wire member is at a temperature below the $M_f$ temperature, however, due to the fact that most adhesives may not adhere to the SMA alloy wire member at such temperatures, the adhesive is preferably applied to the SMA alloy wire member while it is in the austenite state, Where an elastic wire member, such as a support structure made from stainless steel spring wire, is employed, the shape programming described in the preceeding paragraph may, of course, be omitted.

After application of the polymeric cladding at steps 118 and 120, or after the adhesive is applied at step 122, or where step 122 is conducted at a temperature below the $M_f$ temperature of the SMA alloy, the SMA wire is then exposed to a temperature excursion to above the $A_f$ temperature of the SMA alloy at step 114 so that the SMA alloy wire member recovers its programmed shape at step 116. Where an elastic wire member is employed, it is not sensitive to temperature excursions and the temperature excursion step may be omitted.

A tubular substrate, made of, for example, extruded ePTFE, preferably extruded ePTFE which has been radially deformed from its nominal extruded diameter to an enlarged diameter, or woven polyester, is provided at step 123. The wire member in its enlarged shape, which in the case of an SMA wire member is its programmed shape, or in the case of an elastic wire member, in its unstressed state, is concentrically engaged about the tubular substrate at step 124, and joined to the tubular substrate at step 126 by thermally bonding the adhesive or the polymeric cladding to the abluminal or luminal surface of the tubular substrate. It is preferable that step 126 be conducted while the tubular substrate is supported by a support mandrel and that the SMA alloy wire member is retained in intimate contact with a surface of the tubular substrate with at least a portion of the wire member. The wire member, either in its clad or unclad state, may be retained in intimate contact against either by tension wrapping the wire member or by an external covering wrap of a release material, such as polytetrafluoroethylene tape, to cover at least a portion of the wire member.

After the wire member is joined to the tubular substrate, the assembly may optionally be sterilized at step 128, such as by exposure to ethylene oxide for a time and under appropriate conditions to sterilize the assembly. Where an SMA alloy wire member is employed, the assembly is then exposed to a temperature below the $A_s$ temperature of the SMA alloy wire member at step 130 and the assembly is mechanically deformed to a smaller diametric profile at step 132. Where an elastic wire member is employed, the assembly is mechanically deformed to a smaller diametric profile at step 132 largely independent of temperature conditions. Step 132 may be performed by any suitable means to reduce the diametric profile of the assembly, such as by drawing it through a reducing die, manually manipulating the assembly to a reduced diametric profile, or folding the device. The reduced profile assembly is then loaded onto a delivery catheter and covered with a restraining sheath at step 134. Once loaded onto a delivery catheter and covered with a restraining sheath to prevent shape recovery. In the case where the wire member is an SMA alloy, loading the assembly onto a delivery catheter and covering with a restraining sheath requires that step 134 be performed at a temperature below the $A_s$ temperature of the SMA alloy wire in order to prevent thermoelastic recovery of the SMA alloy wire member. Where, however, the wire member is fabricated of an elastic material, the loading step 134 is not largely temperature sensitive and may be performed at room temperature. While the wire member will exert shape recovery forces at room temperature, e.g., above the $A_s$ temperature of the SMA alloy wire employed, the restraining sheath of the delivery catheter will prevent the SMA alloy wire member from recovering its programmed shape and carrying the tubular substrate to the programmed shape of the SMA alloy wire member. Optionally, the sterilization step 128 may also be performed after the assembly is loaded onto the delivery catheter at step 134.

While the present invention has been described with reference to its preferred embodiments and the best mode known to the inventor for making the inventive shape memory alloy supported intraluminal graft, it will be appreciated that variations in material selection for the polymer cladding, for the shape memory alloy, or process variations, such as the manner of winding the polymer clad support wire member about either a winding mandrel or a tubular member, or times and conditions of the manufacturing steps, including material selection, may be made without departing from the scope of the present invention which is intended to be limited only by the appended claims.

What is claimed is:

1. An endoluminal prosthesis, comprising an elongate support wire member joined alone an entire length thereof to at least one surface of a strip of polymer cladding, the joined support wire member and polymer cladding being helically wrapped into an open cylindrical structure such that adjacent windings of the polymer cladding have overlapping regions that are bonded to one another forming said prosthesis.

2. The endoluminal prosthesis according to claim 1, wherein the polymer cladding completely surrounds the support wire member along its length.

3. The endoluminal prosthesis according to claim 1, wherein the polymer cladding comprises a longitudinally extending recess and wherein the support wire member is positioned within said longitudinally extending recess.

4. The endoluminal prosthesis according to claim 1, wherein the polymer cladding comprises a material selected from the group consisting of polytetrafluoroethylene, polyurethane, polyethylene, polypropylene, polyamide, polyimide, polyester, polyfluoroethylenes, silicone, fluorinated polyolefin, fluorinated ethylene/propylene copolymer, perfluoroalkoxy fluorocarbon, ethylene/tetrafluoroethylene copolymer, and polyvinylpyrrolidone.

5. The endoluminal prosthesis according to claim 1, wherein the support wire member comprises a material selected from the group consisting of shape memory alloys, biocompatible spring steels, biocompatible spring metal alloys, and carbon fibers.

6. The endoluminal prosthesis according to claim 1, wherein the support wire member comprises a shape memory alloy with a pre-programmed austenite dimensional state.

7. The endoluminal prosthesis according to claim 1, wherein the support wire member is in the form of a planar ribbon.

8. The endoluminal prosthesis according to claim 1, wherein the polymer cladding has a quadrilateral cross-sectional configuration.

9. The endoluminal prosthesis according to claim 8, wherein the wire member has a quadrilateral cross-sectional configuration.

10. The endoluminal prosthesis according to claim 1, wherein the wire member has a circular cross-sectional configuration.

11. The endoluminal prosthesis according to claim 10, wherein the polymer cladding has a circular cross-sectional configuration.

12. The endoluminal prosthesis according to claim 10, wherein the polymer cladding has a triangular cross-sectional configuration.

13. The endoluminal prosthesis according to claim 12, wherein the polymer cladding in cross-section further comprises a hemispherical recess.

14. The endoluminal prosthesis according to claim 10, wherein the polymer cladding in cross-section has a main body portion with a circular cross-sectional configuration and at least one projection extending radially outward therefrom.

* * * * *

UNITED STATES PATENT AND TRADEMARK OFFICE
CERTIFICATE OF CORRECTION

PATENT NO. : 6,790,226 B2
DATED : September 14, 2004
INVENTOR(S) : Tarun J. Edwin et al.

It is certified that error appears in the above-identified patent and that said Letters Patent is hereby corrected as shown below:

Column 12,
Line 42, change the word "alone" to -- along --

Signed and Sealed this

Twenty-eighth Day of June, 2005

JON W. DUDAS
*Director of the United States Patent and Trademark Office*